United States Patent [19]

Helberg

[11] 4,067,921
[45] Jan. 10, 1978

[54] PRIMARY ADJUNCT, CONTINUOUS DIENE PROCESS

[75] Inventor: Gunnar I. Helberg, Lake Jackson, Tex.

[73] Assignee: The Dow Chemical Company, Midland, Mich.

[21] Appl. No.: 747,584

[22] Filed: Dec. 6, 1976

[51] Int. Cl.$^2$ .................... C07C 11/16; C07C 7/00
[52] U.S. Cl. .................... 260/680 R; 260/677 R; 260/681.5 R
[58] Field of Search ............. 208/67, 130; 260/677 R, 260/680 R

[56] References Cited

U.S. PATENT DOCUMENTS

| | | | |
|---|---|---|---|
| 3,113,164 | 12/1963 | Mathis et al. | 260/680 R |
| 3,179,709 | 4/1965 | Baumann | 260/680 R |
| 3,328,480 | 6/1967 | Begley et al. | 260/681.5 |
| 3,342,890 | 9/1967 | Croce | 260/680 R |
| 3,345,285 | 10/1967 | Hutto | 260/677 R |
| 3,349,147 | 10/1967 | Clay et al. | 260/680 R |
| 3,505,422 | 4/1970 | Brewer et al. | 260/680 R |

Primary Examiner—Veronica O'Keefe
Attorney, Agent, or Firm—G. R. Plotecher

[57] ABSTRACT

$C_n$ dienes are efficiently separated and produced from a $C_n$ hydrocarbon feed stream, wherein n is 4-8. For example, 1,2- and 1,3-butadienes are separated and produced from a $C_4$ hydrocarbon feed stream comprising $C_4$ alkynes, n- and isobutenes, n- and isobutanes and 1,2- and 1,3-butadienes by sequentially:

a. hydrogenating the $C_4$ alkynes and removing any heavy residue produced thereby;
b. separating the 1,2- and 1,3-butadienes into a first stream and the remaining $C_4$ hydrocarbons into a second stream;
c. removing first the isobutene and second the n- and isobutanes from the second stream; and
d. converting the remaining alkenes of the second stream to 1,2- and 1,3-butadienes and then recycling said butadienes to the first stream of (b).

This process affords greater product flexibility with less physical plant than that afforded by conventional processes.

10 Claims, 6 Drawing Figures

PRIMARY ADJUNCT, CONTINUOUS DIENE PROCESS

BACKGROUND OF THE INVENTION

Field of the Invention

This invention relates to processes for separating dienes from diene-containing hydrocarbon mixtures. In one aspect, this invention relates to processes for separating and producing dienes from said mixtures. In another aspect, this invention relates to continuous said processes.

DESCRIPTION OF THE PRIOR ART

Like numerals are employed to designate like parts throughout the drawings. Various items of equipment, such as valves, fittings, and the like, have been omitted from the drawings so as to simplify the description of the prior art. However, those skilled in the art will realize that such conventional equipment can be, and is, employed as desired.

Figure 1:
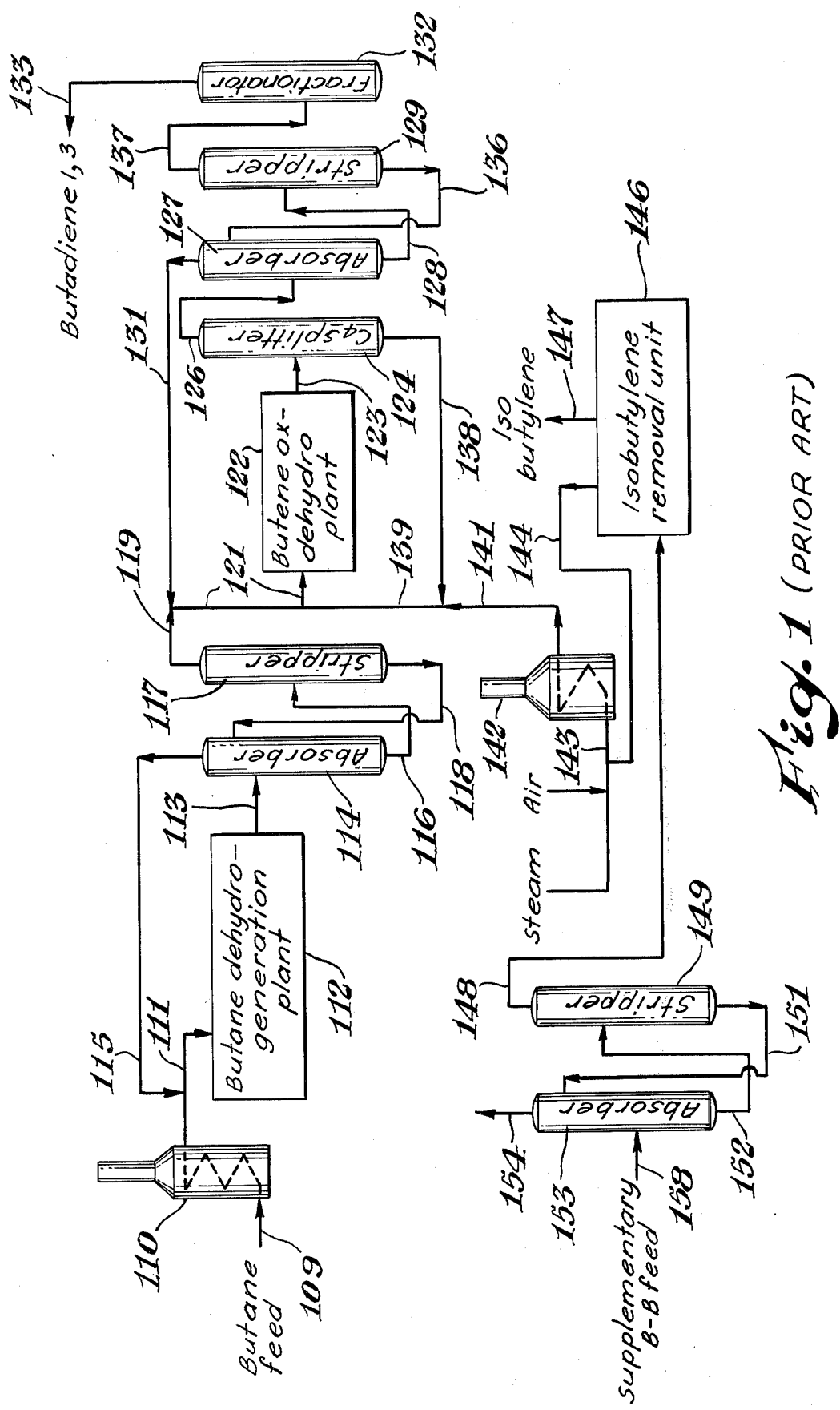
FIG. 1 is a schematic flow diagram illustrating a conventional embodiment of the prior art as applied to the separation and production of butadiene from a $C_4$ hydrocarbon feed stream.
Figure 2:
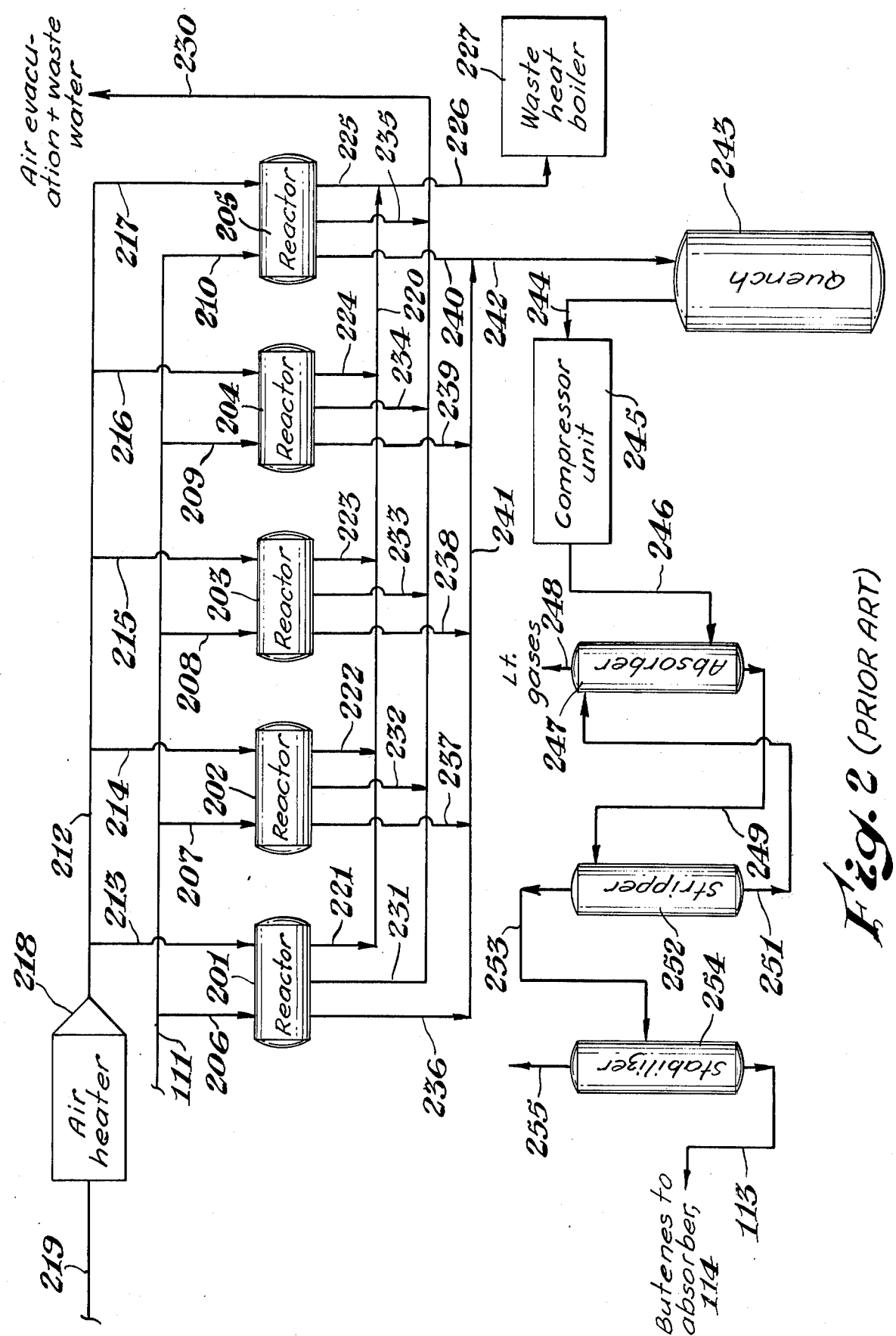
FIG. 2 is a schematic flow diagram illustrating a conventional embodiment of the FIG. 1 dehydrogenation component.

In FIG. 1, a furnace 110, equipped with a butane feed conduit 109, is connected by a conduit 111 to a butane dehydrogenation plant 112 which is illustrated in FIG. 2. A conduit 113 connects an absorber 114 to dehydrogenation plant 112 while a conduit 115 connects absorber 114 to conduit 111. A stripper 117 is connected to absorber 114 by both conduits 116 and 118. Stripper 117 is connected to an oxidation-dehydrogenation plant 122 by conduits 119 and 121, said conduits mating with each other. A splitter 124 is joined by a conduit 123 with oxidation-dehydrogenation plant 122 and a conduit 126 connects splitter 124 with an absorber 127. Absorber 127 is also connected to oxidation-dehydrogenation plant 122 by conduits 121 and 131. Conduits 128 and 136 connect a stripper 129 with absorber 127 while a conduit 137 connects stripper 129 with a fractionator 132. An exit conduit 133 proceeds from fractionator 132.

Referring back to splitter 124, a conduit 138 proceeds from splitter 124 and mates with a conduit 139 which in turn joins conduits 121 and 141. Conduit 141 proceeds from a furnace 142 which is fed by a conduit 143. A conduit 144 connects conduit 143 with an isobutylene removal unit 146 equipped with an exit conduit 147. Isobutylene removal unit 146 is connected to a stripper 149 by a conduit 148. Conduits 151 and 152 connect stripper 149 with an absorber 153, said absorber 153 equipped with both an exit conduit 154 and a feed conduit 158.

Referring now to FIG. 2, dehydrogenation plant 112 of FIG. 1 comprises a series of reactors 201-205 connected to conduit 111 by a series of conduits 206-210. Reactors 201-205 are also connected to a conduit 212 by a series of conduits 213-217. Conduit 212 extends from an air heater 218 which is fed by a conduit 219. A series of conduits 221-225 join reactors 201-205 and a conduit 220. A waste heat boiler 227 is connected to conduit 220 by a conduit 226. An exit conduit 230 also joins reactors 201-205 by a series of conduits 231-235. Reactors 201-205 also join a quench 243 by a series of conduits 236-240 which mate with a conduit 241 which in turn mates with a conduit 242. A compressor unit 245 is connected to quench 243 by a conduit 244, the compressor unit 245 in turn being connected to an absorber 247 by a conduit 246. Absorber 247 is equipped with an exit conduit 248 and is joined to a stripper 252 by conduits 249 and 251. A stabilizer 254 is connected to stripper 252 by a conduit 253, said stabilizer 254 having exit conduits 255 and 113.

Figure 3:
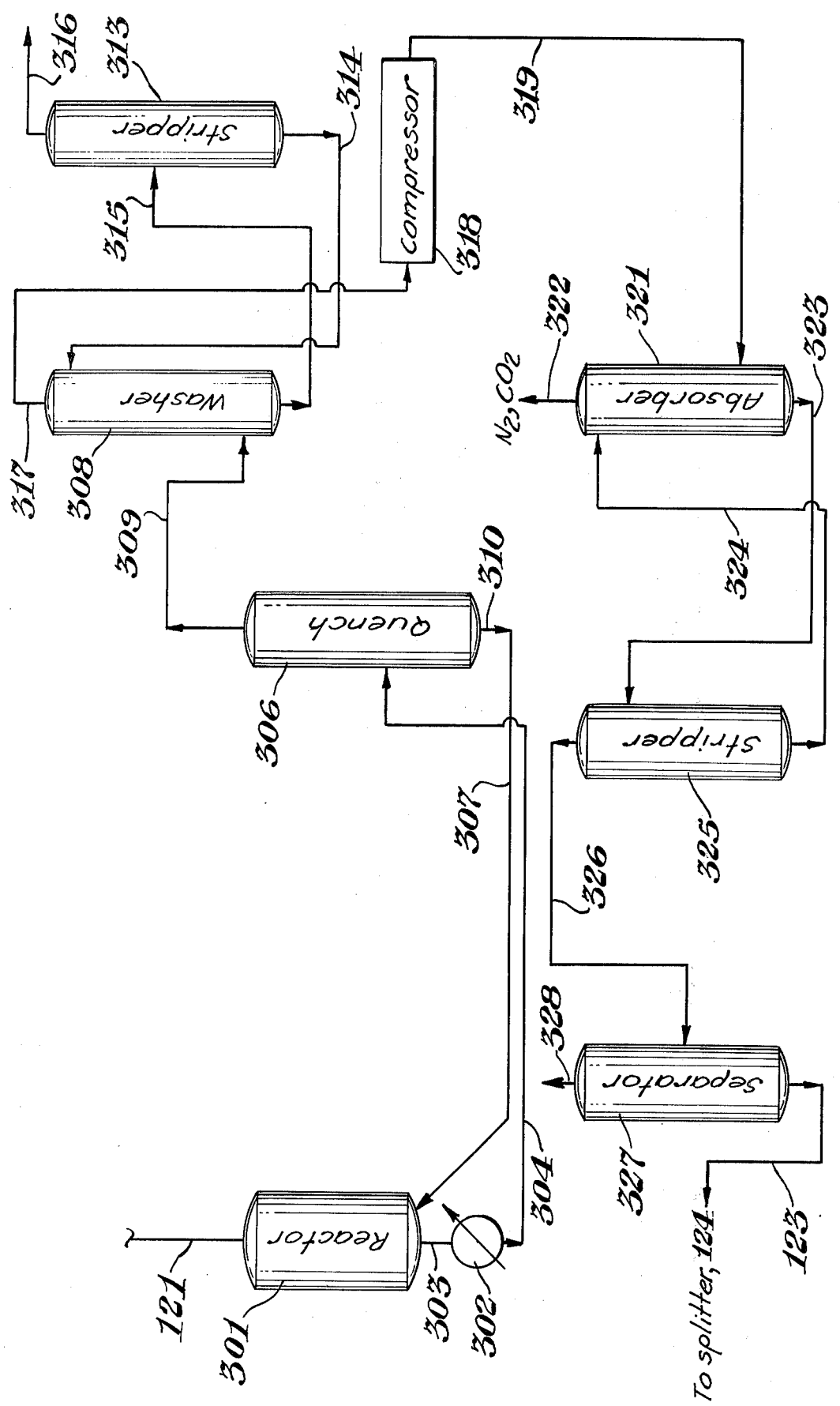
FIG. 3 is a schematic flow diagram illustrating a conventional embodiment of the FIG. 1 oxidative-dehydrogenation component.

Referring now to FIG. 3, oxidation-dehydrogenation plant 122 of FIG. 1 comprises a reactor 301 mating with conduit 121 and connected with a waste heat boiler 302 by a conduit 303. Extending from waste heat boiler 302 is a conduit 304 which connects to a quench 306. Quench 306 is connected to both reactor 301 by conduits 307 and 310 and to a washer 308 by a conduit 309. Washer 308 is connected to a stripper 313 by conduits 314 and 315. A conduit 316 extends from stripper 313. A compressor unit 318 is joined to washer 308 by a conduit 317, compressor unit 318 in turn being joined to an absorber 321 by a conduit 319. Absorber 321 is equipped with an exit conduit 322 and is joined to a stripper 325 by conduits 323 and 324. A conduit 326 connects stripper 325 with a separator 327, the latter equipped with an exit conduit 328. Conduit 123 joins separator 327 with splitter 124 of FIG. 1.

Having thus described the apparatus of this particular prior art embodiment, a $C_4$ hydrocarbon feed stream comprising butane vapors is charged to furnace 110 (of FIG. 1) via conduit 109 and is heated to about 1050°–1150° F. These superheated butane vapors are then transferred via conduit 111 to butane dehydrogenation plant 112.

Referring now to FIG. 2, the superheated butane vapors pass from conduit 111 to reactors 201-205 via conduits 206-210, respectively. Reactors 201-205 are on process, meaning they operate on an automatic cycle-time through the steps of (a) reaction, (b) regeneration, and (c) purge, evacuation and valve switching. Three- and five-bed reactor systems are typical although more or less can be used. In the five-bed reactor system shown here, two reactors are generally in the first step, two in the second step, and one in the third step at any given point in time. Required regeneration energy is supplied in the form of heated air derived by passing air through conduit 219 into air heater 218 and then passing the heated air through conduit 212 into reactors 201-205 via conduits 213-217, respectively. The heat of regeneration developed in reactors 201-205 is transferred through respective conduits 221-225, conduit 220, and conduit 226 to waste heat boiler 227 wherein said heat is recovered. Conduits 231-235 receive from respective reactors 201-205 reaction generated waste water and spent air and transfer same to conduit 230 which in turn removes same from butane dehydrogenation plant 112.

The effluent reactor gas, comprising a mixture of heated butene and unreacted butane vapors, pass from reactors 201-205 to quench 243 via respective conduits 236-240, conduit 241 and conduit 242. Quench 243 recovers a portion of the sensible heat from the transferred gas. The quenched gas is then passed from quench 243 to compressor unit 245 via conduit 244 and compressed therein to about 160 psia. Absorber 247 then receives the compressed gas via conduit 246 and absorbs (in light oil) most of the butenes and unreacted butanes while ejecting light gases (mostly hydrogen) through exit conduit 248. The absorbed butenes and butanes are transferred via conduit 249 into strippper 252 wherein the butenes and butanes are separated from the absorbent; and butenes and butanes are then transferred via conduit 253 to stabilizer 254 and the absorbent is transferred via conduit 251 to absorber 247. From the bottom of stabilizer 254, the butenes are forwarded via conduit 113 to absorber 114 while from the top of stabilizer 254 gases ligher than the butanes are ejected via conduit 255.

Referring back to FIG. 1, the butenes are absorbed by a suitable solvent, such as furfural, in absorber 114 and then forwarded to a stripper 117 via conduit 116. Therein the butene-rich solvent is separated into a butene overhead which is transferred to oxidation-dehydrogenation plant 122 via conduits 119 and 121 and to a lean solvent bottom which is recycled to absorber 114 via conduit 118.

The conventional process generally requires a supplementary butene feed stock to maintain an ongoing butadiene production-separation plant. Said stream is usually a mixture of butenes and butanes and is introduced into the process via conduit 158 which connects with absorber 153 wherein any paraffins in the feed stock are removed in the overhead by exit conduit 154 while the butene-isobutylene stream is preferentially absorbed (again, typically by furfural) and forwarded to stripper 149 through conduit 152. The absorbent is stripped from the butene-isobutylene stream and passed through the bottom of stripper 149 through conduit 151 to absorber 153 while the stripped butene-isobutylene stream is forwarded through the top of stripper 149 through conduit 148 into isobutylene removal unit 146. Therein, cold sulfuric acid selectively absorbs isobutylene and rejects same through exit conduit 147. The spend butene raffinate is forwarded through conduit 144 to conduit 143 wherein same is mixed with steam and air at a steam:air:hydrocarbon molar ratio of approximately 12:3.3:1. The mixture prepared in conduit 143 is then forwarded to furnace 142 wherein it is vaporized and fed through conduit 141 to conduit 139 wherein it is mixed with recycled butene streams passing from splitter 124 through conduit 138. The vaporized butene of conduit 139 is then commingled with the butene vapors of conduit 121 which is fed to butene oxidative-dehydrogenation plant 122.

Referring now to FIG. 3, the steam-air-hydrocarbon mixture is passed through conduit 121 to reactor 301. The butenes of said mixture are therein dehydrogenated to butadiene, said dehydrogenation is exothermic producing a reactor temperature of approximately 1150° F. Consequently, the reaction gases are passed through waste heat boiler 302 via conduit 303 whereby they are cooled to about 385° F. Cooled gases are then passed via conduit 304 to quench 306 wherein they are further cooled to about 110° F. This further cooled stream contains approximately 3 percent by weight carbonyl compounds (oxygenated $C_4$'s) and is thus forwarded via conduit 309 to washer 308 wherein the carbonyls are removed. The carbonyls are collected in the bottoms waste water and forwarded via conduit 315 to stripper 313 wherein the carbonyls are heat stripped, the stripped wash water recycled to washer 308 via conduit 314 and the carbonyls forwarded to a disposal furnace (not pictured) via conduit 316.

The hydrocarbon overhead from washer 308 is forwarded via conduit 317 to compressor unit 318 and then further forwarded to absorber 321 via conduit 319. Noncondensible light gases (nitrogen and carbon dioxide) are rejected from absorber 321 via exit conduit 322 while the absorbed hydrocarbons are forwarded to strippper 325 via conduit 323. $C_4$ hydrocarbons are stripped from the absorbent, again typically light oil, and forwarded to separator 327 via conduit 326 while the absorbent is returned to absorber 323 via conduit 324. Light gases are removed from separator 327 by exit conduit 328 while the $C_4$'s are forwarded to $C_4$ splitter 124 via conduit 123 (refer now to FIG. 1).

$C_4$ splitter 124 separates the $C_4$ stream into a 1-butene and butadiene overhead that is forwarded to absorber 127 via conduit 126 and a butane-2-butene bottom stream that is recycled via conduits 138, 139 and 121 to oxidative-dehydrogenation plant 122. In absorber 127, 1-butene is rejected overhead and recycled to oxidative-dehydrogenation plant 122 via conduits 131 and 121. Stripper 129 receives the butene-free stream from absorber 127 via conduit 128 and therein heat strips the butadiene from the absorbent, generally furfural, and returns the absorbent via conduit 136 to absorber 127. The butadiene is forwarded to a fractionator 132 via conduit 137 wherein it is separated as a monomer of about 99.5 percent purity and collected via conduit 133.

The primary driving force in this butadiene synthesis process is oxidative-dehydrogenation plant 122. This plant is figuratively the "heart" of the process and must be fed fresh butanes/butenes (as described through apparatus 158–141) to perpetrate the plant synthesis activity. As such, the conventional process requires a large capital investment and demonstrates a poor response to market activity. For example, when market demand for butadiene is depressed, operation adjustments generally require a removal of raw feed, such as butenes and/or isobutylenes, from the process which in turn requires operational disruptions and inefficiencies. Moreover, the energy consumption of this conventional process is undesirably high.

Some of these disadvantages in the conventional process are overcome by a variation taught by Hutto et al., U.S. Pat. No. 3,345,285. Therein both ethylene and butadiene are prepared by the disproportionation of propylene and then individually recovered. However, Hutto et al.'s variation requires undesirable amounts of energy and does neither satisfactorily provide market flexibility nor generate sufficient, i.e., high yields, butadiene.

Accordingly, an important object of this invention is to provide a process for synthesizing butadiene that demonstrates a good response to market activity, i.e., market demand for butadiene.

Another object of this invention is to provide a process for synthesizing butadiene that minimizes capital investment and operational expense.

A further object of this invention is to provide a process that maximizes energy conservation.

These and other objects of this invention will be apparent during the course of the following description.

SUMMARY OF THE INVENTION

A novel process for separating and producing $C_n$ dienes from a $C_n$ hydrocarbon feed stream comprising $C_n$ alkynes, $C_n$ n- and isoalkenes, $C_n$ n- and isoalkanes and $C_n$ dienes, wherein n is between 4 and 8 inclusive, is herein disclosed and comprises:

a. hydrogenating the $C_n$ hydrocarbon feed stream to produce a substantially $C_n$ alkyne-free stream comprising $C_n$ n- and isoalkenes, $C_n$ n- and isoalkanes, $C_n$ dienes and heavy residues;

b. removing the heavy residues from the $C_n$ alkyne-free stream to produce a purified $C_n$ stream;

c. separating the purified $C_n$ stream in a first separation zone to produce an extract stream comprising the $C_n$ dienes and a raffinate stream comprising the $C_n$ n-isoalkenes and the $C_n$ n- and isoalkanes;

d. removing the $C_n$ isoalkenes from the raffinate stream and passing a remaining raffinate stream comprising $C_n$ n-alkenes and $C_n$ n-isoalkanes to a second separation zone;

e. separting the remaining raffinate stream in the second separation zone to produce a $C_n$ alkane stream comprising $C_n$ n- and isoalkanes and a $C_n$ alkene stream comprising $C_n$ n-alkenes; and f. converting the $C_n$ alkene stream into a $C_n$ diene stream and recycling said $C_n$ diene stream to the first separtion zone.

This invention derives its uniqueness from the sequence of processing steps and particularly the subordination of the oxidative-dehydrogenation plant in the total process overview. This plant has been reduced from the figurative "heart" of the process to an "expendable kidney", its importance justified by market demand. This novel arrangement of process steps allows rapid and efficient adjustment of the process facility to sudden market changes, it consumes much less energy than the conventional process, and capital and operational expenses in general are substantially below that of the conventional process.

DETAILED DESCRIPTION OF THE INVENTION

Figure 4:
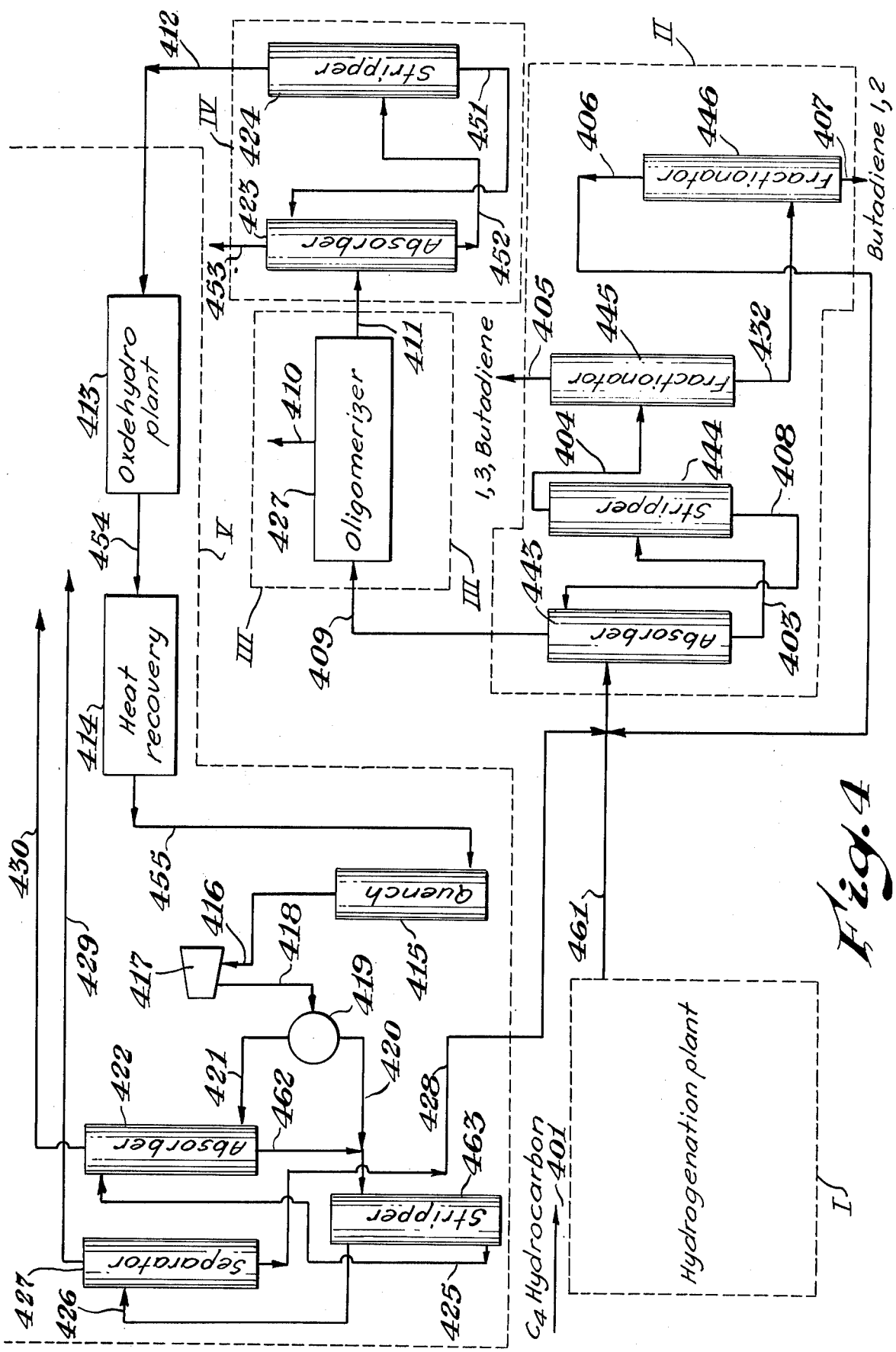
Figure 5:
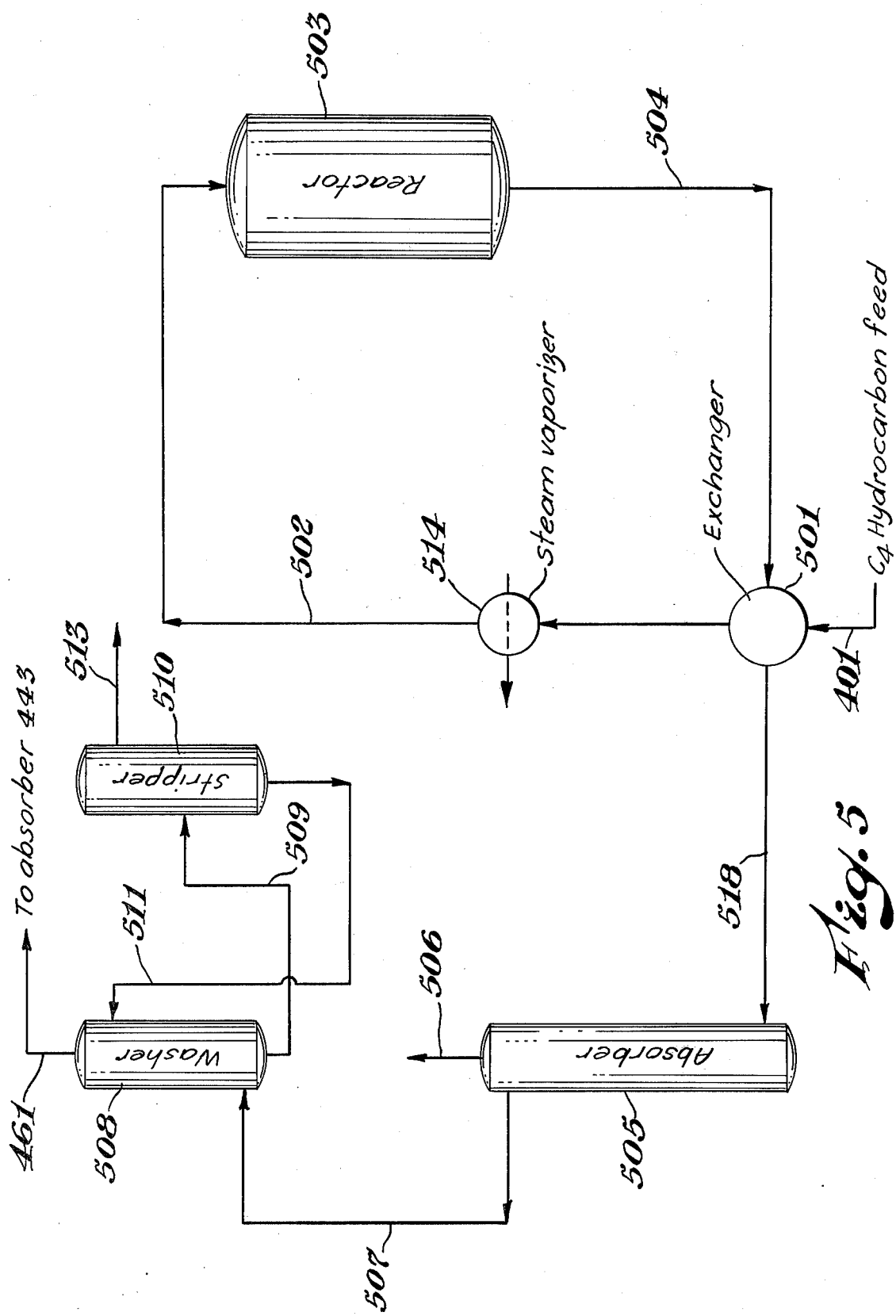
Figure 6:
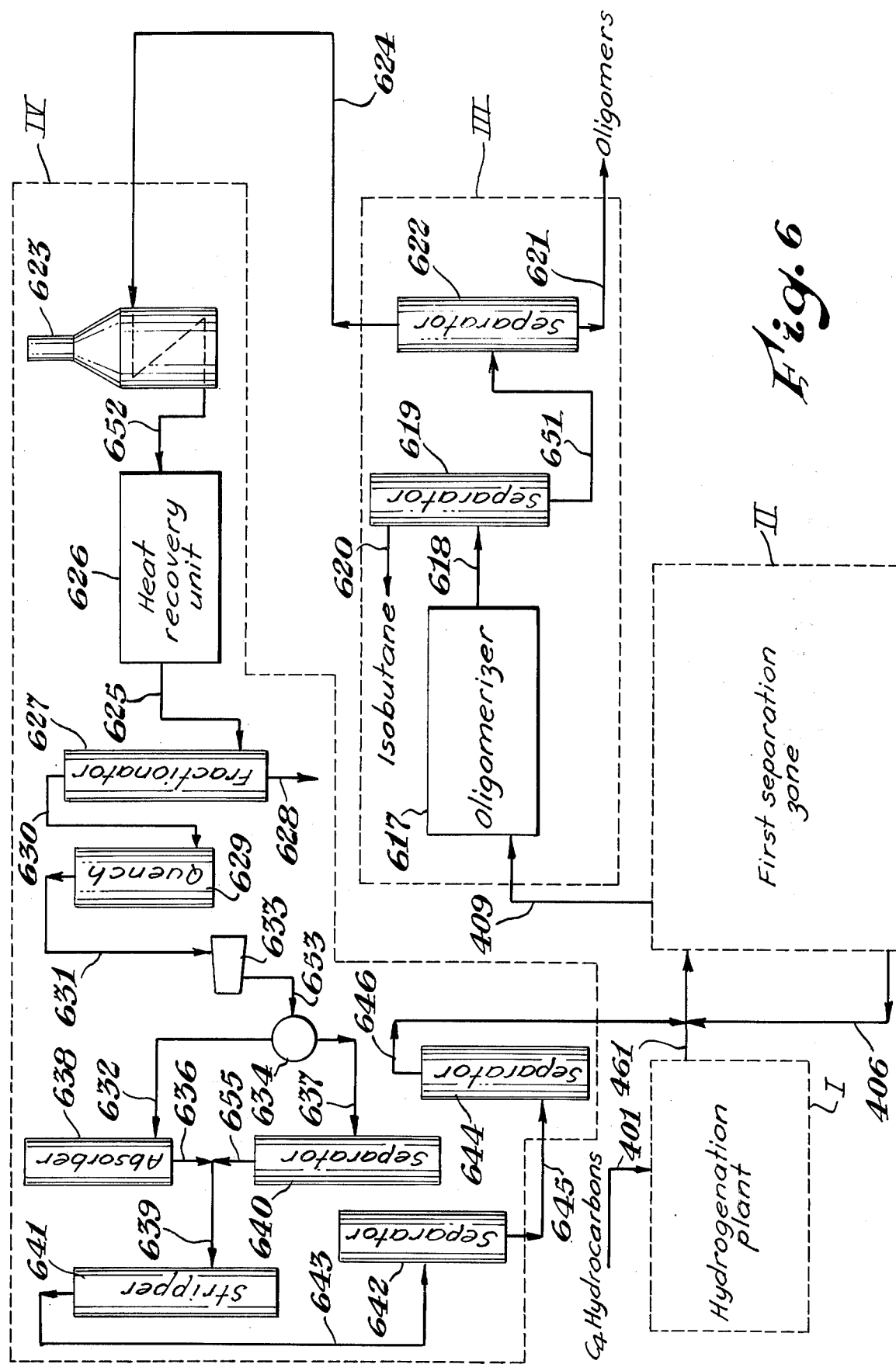

FIG. 4 is a schematic flow diagram illustrating a specific embodiment of the invention as applied to the synthesis of butadiene; and FIG. 5 is a schematic flow diagram illustrating a preferred embodiment of FIG. 1's area I; and FIG. 6 is a schematic flow diagram of another specific embodiment of the invention as applied to the synthesis of butadiene.

As in FIGS. 1-3, like numerals are employed to designate like parts throughout the drawings and various items of equipment, such as valves, fittings and the like, have been omitted from the drawings so as to simplify the description of the invention. However, those skilled in the art will realize that such conventional equipment can be employed as desired.

In FIG. 4, area I represents a hydrogenation zone having a feed conduit 401 and an exit conduit 461.

Referring now to FIG. 5, the area I hydrogenation zone of FIG. 4 comprises a reactor effluent-feed exchanger 501 connected to conduit 401. A reactor 503 is joined to exchanger 501 by a conduit 502 which has disposed at any convenient point thereon a steam vaporizer 514. A conduit 504 connects reactor 503 with exchanger 501 while a conduit 518 connects exchanger 501 with an absorber 505. Absorber 505 is equipped with an exit conduit 506 and is joined to a washer 508 by a conduit 507. Conduits 509 and 511 connect washer 508 with a stripper 510. Exit conduit 461 proceeds from washer 508 while stripper 510 has an exit conduit 513.

Referring back to FIG. 4, exit conduit 461 joins with an absorber 443. Stripper 444 is joined to absorber 443 by conduits 403 and 408. A conduit 404 joins stripper 444 with a fractionator 445, said fractionator being equipped with an exit conduit 405. A fractionator 446 is joined to fractionator 445 by a conduit 432 and a conduit 406 joins fractionator 446 with absorber 443 via conduit 461. An exit conduit 407 extends from fractionator 446. Absorber 443, stripper 444, fractionators 445 and 446 and the connecting and exiting conduits form a first separation zone, depicted as area II.

An oligomerizer 427 (oligomerization zone, area III) is connected to absorber 443 by a conduit 409. Oligomerizer 427 has an exit conduit 410 and is connected to an absorber 423 by a conduit 411. an exit conduit 453 proceeds from absorber 423. Conduits 452 and 451 connect absorber 423 with a stripper 424 while a conduit 412 connects stripper 424 with an oxidative-dehydrogenation plant 413. Said plant 413 is similar to that described in FIG. 3. Absorber 423 and stripper 424 with their connecting conduits comprise a second separation zone, depicted as area IV.

A conduit 454 connects plant 413 with a heat recovery unit 414 which in turn is connected to a quench 415 by a conduit 455. A conduit 416 connects quench 415 with a three-stage compression train 417 which is in turn connected by a conduit 418 to a condenser 419. Condenser 419 is connected to a stripper 463 by a conduit 420 and to an absorber 422 by a conduit 421. Stripper 463 is connected to absorber 422 and a separator 427 by conduits 425 and 426 respectively. Absorber 422 has an exit conduit 430 and is connected to stripper 463 via the mating of a conduit 462 with conduit 420. Separator 427 also has an exit conduit 429 and is connected to absorber 443 by a conduit 428 joining exit conduit 461, thus closing a loop formed by FIG. 1 areas II, III, IV and V. Oxidative-dehydrogenation plant 413, heat recovery unit 414, quench 415, compression train 417, absorber 422, stripper 463, separator 427 and the respective connecting and exiting conduits comprise a dehydrogenation zone, depicted as area V.

In FIG. 6, hydrogenation zone I, described in FIG. 5, has feed conduit 401 and is connected to the first separation zone by conduit 461. Said zone is as described in FIG. IV. Conduit 406 proceeds from area II and mates with conduit 461 while conduit 409 connects area II to an oligomerizer 617 which is in turn connected to a separator 619 by a conduit 618. The separator 619 is equipped with an exit conduit 620 and is connected to a separator 622 by conduit 651. Separator 622 is equipped with an exit conduit 621 and is connected to a pyrolysis furnace 623 by a conduit 624. Oligomerizer 617, separators 619 and 622, and conduits 618, 620, 621 and 651 comprise an oligomerization zone (area III).

A heat recovery unit 626 is connected to furnace 623 by a conduit 652. Conduit 625 connects heat recovery unit 626 to a fractionator 627 which is equipped with an exit conduit 628. A quench 629 is joined to fractionator 627 by a conduit 630 and is itself joined to a three-stage compression train 633 by a conduit 631. A flash unit 634 is joined by a conduit 653 to compression train 633 and conduits 632 and 637 connect flash unit 634 to an absorber 638 and a separator 640 respectively. Exit conduits 636 from absorber 638 and 655 from separator 640 mate with a conduit 639 which in turn joins a stripper 641. Stripper 641 is connected to a separator 642 by a conduit 643 and separator 642 is connected to a separator 644 by a conduit 645. A conduit 646 closes a loop formed by areas II, III and IV by joining separator 644 with the first separation zone via conduit 461. Pyrolysis furnace 623, heat recovery unit 626, fractionator 627, quench 629, compression train 633, flash unit 634, absorber 638, stripper 641, separators 640, 642 and 644, and the respective connecting and exiting conduits comprise a second separation zone (area IV).

Having thus descirbed apparatus of these particular embodiments, conduit 401 of FIGS. 4 and 5 carries a $C_4$ hydrocarbon feed stream comprising $C_4$ alkynes, $C_4$ n- and isoalkenes, $C_4$ n- and isoalkanes and $C_4$ dienes to the hydrogenation zone (area I). Therein, and referring now to FIG. 5 exclusively, the $C_4$ stream is partially vaporized in reactor effluent-feed exchanger 501 with the exchange catalytic reactor gaseous effluent from reactor 503. Exchanger 501 utilizes the heat from the effluent reactor gases to preheat the hydrocarbon feed stream and thereby conserve energy in vaporizer 514. The partially vaporized $C_4$ hydrocarbon stream is then passed into conduit 502 wherein it is mixed with hydrogen (source not pictured) at a molar ratio of approximately 1.5 moles of hydrogen per mole of α-acetylene (the principal $C_4$ alkyne). The resulting mixture is then passed through steam vaporizer 514 wherein it is essentially vaporized completely and heated to a temperature of about 335° F before it is passed on to reactor 503 for catalytic removal of α-acetylene therefrom. The now substantially $C_4$ alkyne-free stream discharged from reactor 503 into conduit 504 is then cross-exchanged with incoming $C_4$ hydrocarbon feed from conduit 401 in reactor effluent-feed exchanger 501. The $C_4$ alkyne-free stream is thus partially cooled and then forwarded to absorption column 505 via conduit 518. Heavy residues formed in reactor 503 are absorbed in light oil from the $C_4$ alkyne-free stream in absorber 505 and the purified (non-absorbed) $C_4$ stream is recovered in an overhead product and forwarded via conduit 507 to washer 508. Exit conduit 506 removes vent (light) gases (hydrogen, methane, ethylene, etc.) from absorber 505. Washer 508 removes the carbonyls from the purified $C_4$ stream. Bottoms consisting mostly of water and traces of carbonyls flow to stripper 510 via conduit 509 wherein the carbonyls are stripped and removed via conduit 513 (to incineration). Conduit 511 returns the stripped water to washer 508. Conduit 461 forwards the overhead (the purified $C_4$ stream with carbonyls removed) to absorber 443 of the first separation zone (area II).

Absorber 443 separates the incoming stream into an extract stream comprising $C_4$ dienes and a raffinate stream comprising $C_4$ alkenes and alkanes (both n- and iso- isomers of each). The $C_4$ dienes, i.e., butadienes, are forwarded via conduit 403 to stripper 444 wherein the absorbent of 433, typically acetonitrile, is returned to absorber 433 via conduit 408 and the dienes are forwarded via conduit 404 to fractionator 445. 1,3-Butadiene is removed via exit conduit 405 while a mixture of 1,2-butadiene, heavy $C_4$'s and unsaturates are forwarded via conduit 432 to fractionator 446. Exit conduit 407 removes warm, 1,2-butadiene therefrom while conduit 406 recycles the $C_4$'s and unsaturates to absorber 443 via conduit 461.

The raffinate stream is forwarded from absorber 443 through conduit 409 to oligomerizer 427. Therein, isobutene is separated therefrom and removed via conduit 410 while the remaining raffinate stream is forwarded via conduit 411 to absorber 423 and the second separation zone (area IV).

Absorber 423 separates the remaining raffinate stream into a $C_4$ alkane stream which is removed via exit conduit 453 and a $C_4$ alkene stream which is forwarded via conduit 452 to stripper 424. Therein, absorbent (typically acetonitrile) is stripped from the $C_4$ alkene stream and returned to absorber 423 via conduit 451 while the $C_4$ alkene stream is forwarded via conduit 412 to oxidative-dehydrogenation plant 413.

The location of the second separation zone at this point in the process is important. Such location allows both use of optimum (smallest) size separation equipment, thus minimizing operating and capital expense, and effective $C_4$ alkane control. The latter is especially important, for if the $C_4$ alkanes accumulate, they will inhibit butadiene production and separation and will eventually necessitate interruption of the continuous process. Usually only about 45 percent of the $C_4$ alkanes need by extracted from the $C_4$ stream received from conduit 411 in order to control this accumulation although more can be extracted if desired. However, further extraction is generally undesirable for the additional utility and capital expense required does not justify the benefit received.

Within plant 413, the $C_4$ alkene stream is mixed with steam, an oxygen-containing gas (typically air) and carbon monoxide at an elevated temperature (between about 1080° F and about 1180° F) in a steam:gas:carbon monoxide:hydrocarbon mass ratio between about 3.5:1:0.1:1 and about 4:1.3:0.2:1 and at a pressure between about 1 and about 2 atmospheres. The conversion of $C_4$ alkenes to $C_4$ dienes is approximately 75 percent and approximately 87 percent of the converted material is 1,3-butadiene for an approximate overall yield of 65 percent.

The effluent gases are forwarded through conduit 454 to heat recovery unit 414 wherein same are cooled and then forwarded through the conduit 455 to quench 415 wherein the gases are further cooled. The quench gases pass through conduit 416 through three-stage compression train 417 where the gas mixture pressure is increased. Pressurized gas in then forwarded via conduit 418 to condenser 419 wherein a partial condensation of the hydrocarbons is accomplished with cooling water.

The noncondensed hydrocarbon gases exit condenser 419 via conduit 421 and enter absorber 422. Therein the heavier hydrocarbons are absorbed by light oil and fed through conduit 462 to conduit 420 while the lighter hydrocarbon gases and nitrogen are removed overhead via exit conduit 430. Conduit 420 removes the condensed gases from condenser 419 and mixes same with the absorbed $C_4$ hydrocarbons from absorber 422 and conduit 462 and introduces the mixture to stripper 463. Stripper 463 separates $C_4$ hydrocarbon stream from conduit 420 into an absorbent stream which is returned to absorber 422 via conduit 425 and a stripped hydrocarbon stream which is forwarded to separator 427 via conduit 426. Light gases are removed therein via exit conduit 429 while the bottoms are recycled via conduit 428 to conduit 461 and the first separation zone. This closes the process loop.

In the embodiment depicted in FIG. 6, a $C_4$ hydrocarbon feed stream is fed into the hydrogenation zone (area I) via conduit 401 and the purified $C_4$ hydrocarbon stream is removed therefrom via conduit 461 to the first separation zone (area II). Areas I and II are as depicted in FIGS. 4 and 5. Oligomizer 617 receives the raffinate from the first separation zone via conduit 409. Therein isobutene and approximately 70 percent of the 1-butene within the raffinate stream are converted in a liquid hase catalytic system to produce di-, tri-, and tetraisobutene. The reactor effluent flows through conduit 618 to separator 619 wherein isobutane is removed via exit conduit 620 and the remaining stream is forwarded through conduit 651 to separator 622. The oligomers are removed via exit conduit 621 while a stream comprising n-butane and n-butene is passed overhead through conduit 624 to furnace 623.

The n-butane and n-butene stream is mixed therein with steam:hydrocarbon mass ratio between about 0.7:1 and about 1.5:1 at a temperature between about 1480° and about 1590° F and a pressure between about 1.5 and about 2 atmospheres. The hydrocarbons are then cracked with furnace 623 with the effluent passed via conduit 652 to heat recovery unit 626. The cooled effluent passes therefrom via conduit 625 to fractionator 627 wherein the heavy fraction of $C_7$-$C_{10}$ is separated and removed via exit conduit 628 while the remainder of the stream containing alkanes, alkenes, dialkenes and aromatics is passed overhead through conduit 630 to quench 629. The quench overhead passes through conduit 631 to three-stage compression train 633. The compressed stream passes to flash unit 634, via conduit 653, wherein the stream is separated into a liquid and a gas phase; the vapor phase passes through conduit 632 and the liquid phase passes through conduit 637. Separator 640 receives the liquid phase, removes benzene therefrom (via means not pictured) and forwards the overhead $C_4$ hydrocarbons through conduits 655 and 639 to stripper 641. Absorber 638 receives the vapors from conduit 632 and an ethylene-methane fraction is removed overhead (not pictured) while the $C_4$ hydrocarbons, aromatics and propylene are absorbed in light oil and forwarded through conduits 636 and 639 to stripper 641. The $C_4$ hydrocarbons, aromatics and propylene are heat stripped from the absorbent and forwarded via conduit 643 to separator 642. Therein propylene is separated as overhead (not pictured) and conduit 645 transports a $C_4$ hydrocarbons and aromatics stream to separator 644. Here the aromatics are removed (not pictured) while the balance of the $C_4$ hydrocarbons are passed as overhead distillate through conduit 646 and combined with the streams in conduits 461 and 406 and then forwarded to the first separator zone (area II).

As is evident from a comparison of FIGS. 4 and 6, the embodiment of FIG. 6 differs from the embodiment of FIG. 4 by the presence of pyrolysis furnace 623 and the absence of oxidative-dehydrogenation plant 413. The presence of furnace 623 provides a variety of valuable co-products, such as propylene, aromatics, etc., and the need for extractive distillation (FIG. 4, area IV) is circumvented. Only a separator (619 in FIG. 6) is required and this is preferably upstream of separator 622, as depicted in FIG. 6. In addition, this separator need only remove, i.e., control the accumulation, of isobutanes whereas the second separation zone of FIG. 4, and with respect to the embodiment depicted therein, must control the accumulation of both isobutane and n-butane. In other words, the presence of furnace 623 eliminates the need to control n-butane accumulation.

The isobutene removal can be had by any of sevral processes whose technology is established, such as oligomerizer 427 shown in FIG. 4. However, an oligomerizer at this point is preferable to most other known technology, such as an isobutene monomer recovery unit, because the former requires a lower capitol investment and can be operated less expensively than the latter. Moreover, the former circumvents the need of extracting with acid which can create brine waste problems.

By placing the oxidative-dehydrogenation unit in a subordinate role, the overall process achieves greater flexibility in its ability to respond to sudden changes in the marketplace. For example, when a strong demand for butadiene exists the process can be conducted as described in FIGS. 4 and 5. When the demand for butadiene is slack, the invention can be conducted such that the oxidative-dehydrogenation unit is circumvented thus freeing the raw materials for other products, reducing butadiene output, and reducing utility consumption.

This process is particularly applicable to and has been described in terms of separating and reducing butenes and butadiene but is also applicable to separating and producing such mixtures as isoamylenes and isoprene, cyclopentene and cyclopentadiene, n-amylene and piperylene and higher alkenes, such as hexenes and heptenes from the corresponding, more unsaturated products.

A skilled artisan will recognize that the description of this invention's disclosed embodiments omits numerous elements typically found in a complete commercial plant. This has been done so in the interest of brevity and lucidity. Variations can be had, such as substituting distillation for solvent extraction in the sparation steps, variations in condensers, and the like. However, since the invention does not lie in the specific types of hydrogenation, dehydrogenation, absorbtion, etc. units, these variations are within the scope of this invention.

Specific Embodiments

EXAMPLE 1

In an example of the operation of this invention according to FIG. 4, the stream fed to the hydrogenation zone is a $C_4$ hydrocarbon feed stream originating from the thermal cracking of a wide range naphtha having a boiling range between about 350° and about 550° F. The operating conditions of the various units of the $C_4$ hydrotreating, separation, and raffinate systems are given in Table I and a material balance is reported in Table II, the stream numbers corresponding to the conduit numbers in FIGS. 4 and 5.

TABLE I

| OPERATING CONDITIONS | |
|---|---|
| 1. REACTOR 503 | |
| Inlet: | 49.7 psia, 350° F Dow Type K Catalyst |
| Outlet: | 45.2 psia, 405° F Hydrogen:Acetylene Ratio 2:1 |
| 2. ABSORBER 505 | |
| Inlet: | 39.7 psia, 130° F |
| Overhead: | 35 psia, 46.4° F |
| Bottoms: | 38 psia, 139.8° F |
| 3. ACETONITRILE ABSORBER 443 | |
| Overhead: | 79.6 psia, 118.4° F |
| Bottoms: | 92.4 psia, 250° F |
| 4. ACETONITRILE STRIPPER 444 | |
| Overhead: | 79.6 psia, 118.4° F |
| Bottoms: | 82.5 psia, 282° F |
| 5. FRACTIONATOR 445 | |
| Overhead: | 56.9 psia, 96.8° F |
| Bottoms: | 64.0 psia, 118.4° F |
| 6. FRACTIONATOR 446 | |
| Overhead: | 49.8 psia, 102° F |
| Bottoms: | 56.9 psia, 136° F |
| 7. OLIGOMERIZER 427 | |
| Farbenfabriken Bayer Liquid Phase Catalyst | |
| Reactor Conditions: | 294 psia, 212° F |
| 8. ABSORBER 423 | |
| Overhead: | 80 psia, 110° F |
| Bottoms: | 95 psia, 260° F |
| 9. STRIPPER 424 | |
| Overhead: | 74 psia, 112° F |
| Bottoms: | 79 psia, 290° F |
| 10. OXIDATIVE-DEHYDROGENATION PLANT 413 | |
| Dow Modified Type B Catalyst | |
| Reactor Pressure: | 30 psia |
| Inlet Temperature: | 685° F |
| Outlet Temperature: | 1100° F |

TABLE I-continued
OPERATING CONDITIONS

| | Stream:Air:HC | |
|---|---|---|
| | Molar Ratio: | 12.6:2.4:1 |
| 11. | ABSORBER 422 | |
| | Overhead Vapor: | 154 psia, 109.5° F |
| | Bottoms: | 157.7 psia, 141° F |
| 12. | STRIPPER 463 | |
| | Reflux Drum: | 110 psia, 153° F |
| | Bottoms: | 122 psia, 644.3° F |
| 13. | SEPARATOR 427 | |
| | Reflux Drum: | 238 psia, 100° F |
| | Reboiler Vapor: | 242 psia, 216.4° F |

TABLE II
MATERIAL BALANCE[1] (Based on FIG. 4)

| Component | 401 | 518 | 403 | 404 | 405 | 406 | 407 |
|---|---|---|---|---|---|---|---|
| Hydrogen | 33 | — | — | — | — | — | — |
| Nitrogen | — | — | — | — | — | — | — |
| Carbon Monoxide | 5 | 5 | — | — | — | — | — |
| Oxygen | — | — | — | — | — | — | — |
| Methane | 106 | 106 | — | — | — | — | — |
| Ethylene | 5 | 5 | — | — | — | — | — |
| Carbon Dioxide | — | 17 | — | — | — | — | — |
| Propane | 53 | 53 | — | — | — | — | — |
| Isobutane | 523 | 523 | — | — | — | — | — |
| Isobutene | 9,584 | 9,584 | 7 | 7 | 7 | — | — |
| 1-Butene | 7,949 | 8,366 | 7 | 7 | 7 | — | — |
| 1,3-Butadiene | 24,360 | 24,066 | 31,099 | 31,099 | 30,788 | 311 | — |
| n-Butane | 2,831 | 2,831 | — | — | — | — | — |
| trans-2-Butene | 2,480 | 2,480 | 201 | 201 | 72 | 129 | — |
| cis-2-Butene | 2,387 | 2,387 | 592 | 592 | — | 583 | 9 |
| 1,2-Butadiene | 94 | 94 | 87 | 87 | — | — | 86 |
| Vinylacetylene | 431 | — | — | — | — | — | — |
| Water | — | — | 23,756 | — | — | — | — |
| Butadiene Dimer | 51 | 375 | — | — | — | — | — |
| Oligomer | — | — | — | — | — | — | — |
| Total Hydrocarbons | 50,892 | 50,892 | 31,993 | 31,993 | 30,874 | 1,023 | 95 |
| Acetonitrile | — | — | 310,494 | — | — | — | — |

| Component | 408 | 409 | 410 | 411 | 412 | 429 | 428 |
|---|---|---|---|---|---|---|---|
| Hydrogen | — | — | — | — | — | — | — |
| Nitrogen | — | — | — | — | — | 17 | — |
| Carbon Monoxide | — | 1 | — | — | — | — | — |
| Oxygen | — | — | — | — | — | — | — |
| Methane | — | 29 | — | 29 | — | 1 | — |
| Ethylene | — | 3 | — | 3 | — | 7 | — |
| Carbon Dioxide | — | 6 | — | 6 | — | 4 | — |
| Propane | — | 49 | — | 49 | — | 129 | — |
| Isobutane | — | 880 | — | 880 | 484 | 26 | 370 |
| Isobutene | — | 9,577 | — | 71 | 71 | 9 | 212 |
| 1-Butene | — | 8,846 | 1 | 2,653 | 2,653 | 24 | 668 |
| 1,3-Butadiene | — | 156 | — | — | — | 208 | 7,687 |
| n-Butane | — | 4,773 | 2 | 4,771 | 2,624 | 22 | 1,999 |
| trans-2-Butene | — | 3,637 | 2 | 6,025 | 6,025 | 13 | 1,409 |
| cis-2-Butene | — | 3,034 | 3 | 5,422 | 5,422 | 8 | 1,297 |
| 1,2-Butadiene | — | — | — | — | — | — | — |
| Vinylacetylene | — | — | — | — | — | — | — |
| Water | 23,756 | — | — | — | — | — | — |
| Butadiene Dimer | — | — | — | — | — | — | — |
| Oligomer | — | — | 10,913 | 161 | 161 | — | — |
| Total Hydrocarbons | — | 30,991 | 10,921 | 20,070 | 17,440 | 468 | 13,642 |
| Acetonitrile | 310,494 | — | — | — | — | — | — |

[1]All figures are in pounds/hour

EXAMPLE 2

This is an example according to FIG. 6. The operating conditions after the hydrogenation zone are different than those used in Example 1 due to the fact that only a portion of the isobutane component is removed from the system for stabilizing purposes and thus area IV of FIG. 4 is eliminated. In addition, the pyrolysis furnace 623 readily converts normal C₄ butanes and butenes into valuable coproducts, maximizing, in this case, butadiene production (by generating recyclable butenes). Flow sequence can be further modified by substituting another pair of absorber-stripper columns for the reactor 503 and its associated absorber 505 to separate the α-acetylenes from the butadienes and heavy C₄ butenes fraction. The hydrocarbon feed stream is little effected by the mode of operation. Of course, reactor 503 and absorber 505 are illustrated in FIG. 5 and therefore form the basis of this example. The operating conditions of the various units are reported in Table III andthe material balance thereof in Table IV.

TABLE III
OPERATING CONDITIONS

| | | |
|---|---|---|
| 1. | REACTOR 503 | |
| | Dow Type K Catalyst | |
| | H₂/Acetylene Ratio: | 2:1 |
| | Reactor Conditions: | 45.2 psia, 405° F |
| 2. | ABSORBER 505 | |
| | Reflux Drums: | 30 psia, 35.6° F |
| | Reboiler Vapor: | 38 psia, 159.4° F |
| 3. | ACETONITRILE ABSORBER 443 | |
| | Reflux Drum: | 79.6 psia, 118° F |
| | Reboiler Vapor: | 92.4 psia, 264° F |
| 4. | ACETONITRILE STRIPPER 444 | |
| | Reflux Drum: | 79.6 psia, 118° F |
| | Reboiler Vapor: | 83 psia, 287° F |
| 5. | FRACTIONATOR 445 | |
| | Reflux Drum: | 56.9 psia, 96.8° F |
| | Reboiler Vapor: | 64 psia, 118.4° F |
| 6. | FRACTIONATOR 446 | |
| | Reflux Drum: | 49.8 psia, 102° F |
| | Reboiler Vapor: | 56.9 psia, 136° F |
| 7. | OLIGOMERIZER 617 | |
| | Farbenfabriken Bayer Liquid Phase Catalyst | |
| | Reactor Conditions: | 294 psia, 212° F |
| 8. | SEPARATOR 619 | |
| | Reflux Drum: | 96 psia, 79.5° F |
| | Reboiler Vapor: | 101.8 psia, 164° F |
| 9. | SEPARATOR 622 | |
| | Reflux Drum: | 80 psia, 128.8° F |
| | Reboiler Vapor: | 89 psia, 352.7° F |

TABLE III-continued

OPERATING CONDITIONS

10. PYROLYSIS FURNACE 623
    - Steam/HC Mass Ratio: 1:1
    - Outlet Pressure: 30 psia
    - Outlet Temperature: 1480–1590° F
11. HEAT RECOVERY UNIT 626
    - Steam Generated at 250 psia
12. FRACTIONATOR 627
    - Overhead Vapor: 24.7 psia, 21.3° F
    - Reboiler Vapor: 26.1 psia, 374.3° F
13. QUENCH 629
    - Tower Inlet: 24.7 psia, 221.3° F
    - Tower Outlet: 21.1 psia, 110.3° F
14. COMPRESSOR 633
    - 1st Stage Inlet: 20.1 psia, 100.3° F
    - 1st Stage Outlet: 37.6 psia, 163.4° F
    - 207 Horsepower
    - 1st Flash: 35.1 psia, 100.3° F
    - 2nd Stage Inlet: 35.1 psia, 100.3° F
    - 2nd Stage Outlet: 81.6 psia, 185.5° F
    - 281 Horsepower
    - 2nd Flash: 79.6 psia, 100.3° F

TABLE III-continued

OPERATING CONDITIONS

- 3rd Stage Inlet: 79.6 psia, 100.3° F
- 3rd Stage Outlet: 165.0 psia, 172.7° F
- 233.6 Horsepower
15. FLASH UNIT: 634:160 psia, 110° F
16. ABSORBER 638
    - Overhead Vapor: 154 psia, 109.5° F
    - Bottoms: 57.7 psia, 141.4° F
17. SEPARATOR 640
    - Reflux Drum: 156 psia, 72.3° F
    - Reboiler Vapor: 163 psia, 363.5° F
18. STRIPPER 641
    - Reflux Drum: 110 psia, 153° F
    - Reboiler Vapor: 122 psia, 644.3° F
19. SEPARATOR 642
    - Reflux Drum: 238 psia, 99.5° F
    - Reboiler Vapor: 242 psia, 216.4° F
20. SEPARATOR 644
    - Reflux Drum: 194 psia, 193.8° F
    - Reboiler Vapor: 202 psia, 291.7° F

TABLE IV

MATERIAL BALANCE[1] (Based on FIG. 6)

| Component | 401 | 518 | 461 | 403 | 404 | 405 | 406 | 407 | 408 |
|---|---|---|---|---|---|---|---|---|---|
| Hydrogen | 33 | — | — | — | — | — | — | — | — |
| Methane | 107 | 107 | 37 | — | — | — | — | — | — |
| Ethylene | 5 | 5 | 4 | — | — | — | — | — | — |
| Ethane | — | 12 | 10 | — | — | — | — | — | — |
| Propylene | 51 | 51 | 49 | — | — | — | — | — | — |
| Isobutane | 527 | 527 | 521 | — | — | — | — | — | — |
| Isobutene | 9,650 | 9,650 | 9,561 | 7 | 7 | 7 | — | — | — |
| 1-Butene | 8,005 | 8,425 | 8,347 | 7 | 7 | 7 | — | — | — |
| 1,3-Butadiene | 24,527 | 24,230 | 24,013 | 26,229 | 26,229 | 26,097 | 132 | — | — |
| n-Butane | 2,850 | 2,850 | 2,820 | — | — | — | — | — | — |
| trans-2-Butene | 2,497 | 2,497 | 2,467 | 211 | 211 | 59 | 152 | — | — |
| cis-2-Butene | 2,404 | 2,404 | 2,359 | 578 | 578 | — | 569 | 9 | — |
| 1,2-Butadiene | 95 | 95 | 87 | 87 | 87 | — | 1 | 86 | — |
| Vinylacetylene | 434 | 1 | — | — | — | — | — | — | — |
| Benzene | — | — | — | — | — | — | — | — | — |
| Water | — | — | — | 17,455 | — | — | — | — | 17,455 |
| Oligomer | — | — | — | — | — | — | — | — | — |
| Toluene | — | — | — | — | — | — | — | — | — |
| Naphthalene | — | — | — | — | — | — | — | — | — |
| Dimer Oil | 62 | 394 | — | — | — | — | — | — | — |
| Total Hydrocarbons | 51,247 | 51,247 | 50,275 | 27,119 | 27,119 | 26,170 | 854 | 95 | — |
| Acetonitrile | — | — | — | 173,898 | 2 | — | — | — | 173,898 |

| Component | 409 | 618 | 620 | 621 | 624 | 625 | 628 | 630 | 631 |
|---|---|---|---|---|---|---|---|---|---|
| Hydrogen | — | — | — | — | — | 134 | — | 134 | 134 |
| Methane | 37 | 37 | 37 | — | — | 2,237 | — | 2,237 | 2,237 |
| Ethylene | 4 | 4 | 4 | — | — | 2,449 | — | 2,449 | 2,449 |
| Ethane | 10 | 10 | 10 | — | — | 258 | — | 258 | 258 |
| Propylene | 49 | 49 | 49 | — | — | 3,464 | — | 3,464 | 3,464 |
| Isobutane | 1,335 | 1,335 | 339 | — | 996 | 996 | — | 996 | 996 |
| Isobutene | 9,616 | 72 | 4 | — | 68 | 68 | — | 68 | 68 |
| 1-Butene | 8,697 | 2,609 | 85 | — | 2,524 | 392 | — | 392 | 392 |
| 1,3-Butadiene | 66 | — | — | — | — | 2,488 | — | 2,488 | 2,488 |
| n-Butane | 4,283 | 4,283 | 6 | 1 | 4,276 | 1,556 | — | 1,556 | 1,556 |
| trans-2-Butene | 3,811 | 6,161 | 5 | 1 | 6,155 | 1,704 | — | 1,704 | 1,704 |
| cis-2-Butene | 2,963 | 5,313 | 1 | 1 | 5,311 | 1,290 | — | 1,290 | 1,290 |
| 1,2-Butadiene | — | — | — | — | — | — | — | — | — |
| Vinylacetylene | — | — | — | — | — | — | — | — | — |
| Benzene | — | — | — | — | — | 1,778 | — | 1,778 | 1,778 |
| Water | — | — | — | — | — | 20,088 | — | 20,088 | — |
| Oligomer | — | 10,998 | — | 10,901 | 96 | 96 | 96 | — | — |
| Toluene | — | — | — | — | — | 423 | 423 | — | — |
| Naphthalene | — | — | — | — | — | 93 | 93 | — | — |
| Oil - $C_{10}$ | — | — | — | — | — | — | — | — | — |
| Total Hydrocarbons | 30,871 | 30,871 | 540 | 10,904 | 19,426 | 39,514 | 612 | 38,902 | 18,814 |
| Acetonitrile | — | — | — | — | — | — | — | — | — |

| Component | 632 | 636 | 637 | 639 | 643 | 645 | 646 |
|---|---|---|---|---|---|---|---|
| Hydrogen | 134 | — | — | — | — | — | — |
| Methane | 2,231 | 33 | 6 | 39 | 39 | — | — |
| Ethylene | 2,415 | 164 | 34 | 198 | 198 | — | — |
| Ethane | 252 | 28 | 6 | 33 | 33 | — | — |
| Propylene | 3,211 | 1,154 | 254 | 1,408 | 1,408 | — | — |
| Isobutane | 800 | 789 | 196 | 984 | 984 | 899 | 896 |
| Isobutene | 54 | 53 | 15 | 68 | 68 | 66 | 66 |
| 1-Butene | 305 | 305 | 87 | 391 | 391 | 381 | 379 |
| 1,3-Butadiene | 1,917 | 1,913 | 572 | 2,484 | 2,484 | 2,440 | 2,423 |
| n-Butane | 1,160 | 1,160 | 395 | 1,556 | 1,556 | 1,547 | 1,524 |
| trans-2-Butene | 1,259 | 1,258 | 445 | 1,703 | 1,703 | 1,694 | 1,668 |
| cis-2-Butene | 933 | 933 | 357 | 1,290 | 1,290 | 1,286 | 1,256 |
| 1,2-Butadiene | — | — | — | — | — | — | — |
| Vinylacetylene | — | — | — | — | — | — | — |
| Benzene | 291 | 293 | 1,487 | 333 | 323 | 323 | — |

TABLE IV-continued
MATERIAL BALANCE[1] (Based on FIG. 6)

| | Stream Number | | | | | | |
|---|---|---|---|---|---|---|---|
| Water | — | — | — | — | — | — | — |
| Oligomer | — | — | — | — | — | — | — |
| Toluene | — | — | — | — | — | — | — |
| Naphthalene | — | — | — | — | — | — | — |
| Oil - $C_{10}$ | — | 40,178 | — | 40,178 | — | — | — |
| Total Hydrocarbons | 14,962 | 48,261 | 3,854 | 50,665 | 10,477 | 8,636 | 8,212 |
| Acetonitrile | — | — | — | — | — | — | — |

[1]All figures are in pounds/hour.

Control with Comparison Tables

Table V reports a material balance in pounds/hour based upon FIG. 1. Table VI reports a BTU, raw material and conversion comparison between said FIG. 1 process and the invention per FIG. 4. The Table VI report demonstrates the efficiency of the invention, said invention consuming approximately 45 percent of the total utility consumption of the prior art process.

Tables VII and VIII report comparisons of energy consumption and environmental impact between the invention per FIGS. 4 and 6, respectively, and the prior art per FIGS. 1 and 2. In each case, the invention requires no fresh (supplementary) feed (FIG. 1, conduit 158), and consumes less energy for by-products, and less steam, power, cooling water, fuel and invested capital, all on a pound for pound basis, than the prior art. Moreover, the invention has a better environmental impact than the prior art.

Table IX is a comparison between the invention per FIG. 4 and the process of Hutto et al. and also represents a proportional breakdown of the figures reported in Table VI. Here too, the invention demonstrates superior efficiency.

TABLE V
MATERIAL BALANCE[1] (Based on FIG. 1)

| Component | Stream No. | | | | | |
|---|---|---|---|---|---|---|
| | 109 | 113 | 115 | 119 | 121 | 126 |
| Hydrogen | — | — | — | — | — | — |
| Nitrogen | — | — | — | — | 269,120 | — |
| Carbon Monoxide | — | — | — | — | — | — |
| Oxygen | — | — | — | — | 81,656 | — |
| Methane | — | — | — | — | — | — |
| Ethylene | — | — | — | — | — | — |
| Carbon Dioxide | — | — | — | — | — | — |
| Propane | — | 38 | 38 | — | 769 | 362 |
| Isobutane | 2,483 | 853 | 686 | 167 | 19,078 | 17,355 |
| Isobutene | — | 2,386 | 1,239 | 1,146 | 576 | 634 |
| 1-Butene | — | 33,519 | 3,975 | 29,544 | 24,733 | 8,556 |
| 1,3-Butadiene | — | 22,194 | 698 | 21,496 | 4,687 | 87,885 |
| n-Butane | 168,510 | 168,830 | 160,000 | 8,779 | 31,073 | 4,997 |
| trans-2-Butene | — | 50,611 | 6,615 | 43,996 | 64,520 | 1,163 |
| cis-2-Butene | — | 40,111 | 2,222 | 37,889 | 59,305 | 21 |
| Pentane | — | 1,157 | — | 1,157 | 1,155 | — |
| Vinylacetylene | — | — | — | — | — | — |
| Water | — | — | — | — | 765,480 | — |
| Butadiene Dimer | — | — | — | — | — | — |
| Oligomer | — | — | — | — | — | — |
| Total Hydrocarbons | 170,993 | 319,699 | 175,473 | 144,174 | 1,322,152 | 120,973 |
| Furfural | — | — | — | — | — | — |

| Component | 131 | 133 | 136 | 137 | 138 | 147 | 158 |
|---|---|---|---|---|---|---|---|
| Hydrogen | — | — | — | — | — | — | — |
| Nitrogen | — | — | — | — | — | — | — |
| Carbon Monoxide | — | — | — | — | — | — | — |
| Oxygen | — | — | — | — | — | — | — |
| Methane | — | — | — | — | — | — | — |
| Ethylene | — | — | — | — | — | — | — |
| Carbon Dioxide | — | — | — | — | — | — | — |
| Propane | 362 | — | — | — | — | — | 1,047 |
| Isobutane | 17,355 | — | — | — | — | — | 17,682 |
| Isobutene | 576 | 58 | — | 58 | — | 5,046 | 7,360 |
| 1-Butene | 8,328 | 228 | — | 228 | 16 | — | 7,967 |
| 1,3-Butadiene | 352 | 87,500 | — | 87,536 | 1,102 | — | — |
| n-Butane | 4,996 | 1 | — | 1 | 17,855 | — | 13,334 |
| trans-2-Butene | 137 | 184 | — | 1,067 | 22,077 | — | 4,893 |
| cis-2-Butene | — | — | — | 64 | 20,842 | — | 7,039 |
| Pentane | — | — | — | — | — | — | 888 |
| Vinylacetylene | — | — | — | — | — | — | — |
| Water | — | — | 86,000 | — | — | — | — |
| Butadiene Dimer | — | — | — | — | — | — | — |
| Oligomer | — | — | — | — | — | — | — |
| Total Hydrocarbons | 32,106 | 87,971 | — | 88,954 | 61,892 | 8,284 | 60,210 |
| Furfural | — | — | 1,572,000 | — | — | — | — |

[1]All figures are in pounds/hour.

TABLE VI

| | INVENTION/ FIG. 4 | PRIOR ART PROCESS/ FIG. 1 |
|---|---|---|
| | Co-Product Butadiene Extraction & Recycling | Oxidation-Dehydrogenation and Butadiene Extraction |
| Total BTUs/LB Butadiene | 42,020 | 57,773 |
| Raw Materials (LB) | 29,407 | 29,500 |

TABLE VI-continued

PRIOR

| | | |
|---|---|---|
| Conversion | 12,613 | 28,273 |

TABLE VII

CATALYTIC DEHYDROGENATION ZONE[1]

| | INVENTION/Figure 4 | PRIOR ART/Figures 1 & 2 |
|---|---|---|
| I. FRESH FEED REQUIREMENTS: | | |
| lb, Butane | — | 1.62 |
| lb, Butene | — | 0.57 |
| TOTAL | — | 2.19 |
| II. CREDITS: | | |
| lb, Isobutene | — | 0.048 |
| lb, Diiso- & Triisobutene | 0.36 | 0.031 |
| III. STEAM: | | |
| lb, 450 psig | 2.22 | 5.37 |
| lb, 235 psig | 2.28 | 6.51 |
| lb, 150 psig | 2.41 | 8.83 |
| lb, 30 psig | 0.25 | −6.23 |
| NET | 7.16 | 14.48 |
| IV. POWER, kwh | 0.06 | 0.14 |
| V. COOLING WATER, gal. | 24.4 | 182.8 |
| VI. CONDENSATE, lb | −7.02 | −19.61 |
| VII. FUEL GAS, BTU | 3,175.00 | 8,995.00 |
| VIII. AIR, SCF | 0.76 | 0.66 |
| IX. INVESTED CAPITAL, $ | 0.1271 | 0.2041 |
| X. ENVIRONMENTAL IMPACT: | | |
| Raw Waste Load, gal. | 0.145 | 1.20 |
| | | $2.97 (10^{-3})$[2] |

[1] All data expressed in units/pound of butadiene.
[2] Figure 2, conduit 230 air evacuation and waste water.

TABLE VIII

PYROLYSIS DEHYDROGENATION ZONE[1]

| | INVENTION/Figure 6 | PRIOR ART/Figures 1 & 2 |
|---|---|---|
| I. FRESH FEED REQUIREMENTS: | | |
| lb, Butane | — | 1.62 |
| lb, Butene | — | 0.57 |
| TOTAL | — | 2.19 |
| II. CREDITS: | | |
| lb, Isobutene | — | 0.048 |
| lb, Diiso- & Triisobutene | 0.417 | 0.031 |
| lb, Ethylene | 0.093 | — |
| lb, Propylene | 0.131 | — |
| lb, Benzene | 0.067 | — |
| III. STEAM: | | |
| lb, 450 psig | 1.92 | 5.37 |
| lb, 235 psig | −0.91 | 6.51 |
| lb, 150 psig | 5.56 | 8.83 |
| lb, 30 psig | 1.32 | −6.23 |
| NET | 7.89 | 14.48 |
| IV. POWER, kwh | 0.044 | 0.14 |
| V. COOLING WATER, gal. | 41.19 | 182.80 |
| VI. CONDENSATE, lb | −5.75 | −19.61 |
| VII. Fuel Gas, Btu | 2,602.0 | 8,995.0 |
| VIII. AIR, SCF | 0.76 | 0.66 |
| IX. INVESTED CAPITAL, $ | 0.139 | 0.2041 |
| X. ENVIRONMENTAL IMPACT: | | |
| BOD Waste Load, gal. sd.18 | 0.145 | 1.20 |
| | $2.8 (10^{31.4})$ | $2.97 (10^{31.3})$[2] |

[1] All data expressed in units/pound of butadiene.
[2] Figure 2, conduit 230 air evacuation and waste water.

| INVENTION/FIG. 4 | ART PROCESS/FIG. 1 |
|---|---|
| Co-Product Butadiene Extraction & Recycling | Oxidation-Dehydrogenation and Butadiene Extraction |

TABLE IX[1]

| INVENTION/Figure 4 | | HUTTO ET AL. PROCESS | |
|---|---|---|---|
| I. ALKYNE REMOVAL | | I. PROPYLENE DISPROPORTIONATION | |
| Steam, 400 psig | 0.22 lb | Steam, 400 psig | — |
| 150 psig | 0.51 lb | 150 psig | — |
| 30 psig | 0.048 lb | 30 psig | 0.753 lb |
| Power, kwh | 0.0041 | Power, kwh | 0.027 |
| Cooling Water, gal. | 6.74 | Cooling Water, gal. | 6.25 |
| Fuel, BTU | 176.0 | Fuel, BTU | 443.0 |
| Condensate, lb | −1.36 | Condensate, lb | — |
| II. BUTADIENE EXTRACTION | | II. BUTADIENE EXTRACTION | |
| Steam, 150 psig | 1.01 lb | Steam, 150 psig | 1.751 lb |
| 30 psig | 0.055 lb | 30 psig | — |
| Power, kwh | 0.0021 lb | Power, kwh | 0.0007 lb |

TABLE IX[1]-continued

| INVENTION/Figure 4 | | | | HUTTO ET AL. PROCESS | | | |
|---|---|---|---|---|---|---|---|
| Cooling Water, gal. | | | 3.09 | Cooling Water, gal. | | | 8.343 |
| Fuel, BTU | | | — | Fuel, BTU | | | — |
| Process Water, gal. | | | 0.11 | Process Water, gal. | | | 0.20 |
| condensate, lb | | | — | Condensate, lb | | | −2.78 |
| III. BUTENE EXTRACTION | | | | III. BUTENE EXTRACTION | | | |
| Steam, 150 psig | | | 0.84 lb | Steam, 150 psig | | | 1.243 |
| 30 psig | | | 30 psig | | | | |
| Power, kwh | | | 0.0047 | Power, kwh | | | 0.0015 |
| Cooling Water, gal. | | | 0.664 | Cooling Water, gal. | | | 0.944 |
| Fuel, BTU | | | — | Fuel, BTU | | | — |
| Condensate, lb | | | −0.76 | Condensate, lb | | | −2.37 |
| IV. OLIGOMERIZATION | | | | IV. ISOBUTENE REMOVAL | | | |
| Steam, 150 psig | | | 0.053 lb | Steam, 150 psig | | | 1.318 lb |
| 30 psig | | | 0.001 lb | 30 psig | | | 0.169 lb |
| Power, kwh | | | 0.0021 | Power, kwh | | | 0.014 |
| Cooling Water, gal. | | | 0.837 | Cooling Water, gal. | | | 3.694 |
| Fuel, BTU | | | — | Fuel, BTU | | | — |
| Condensate, lb | | | — | Condensate, lb | | | — |
| V. OXIDATION-DEHYDROGENATION | | | | V. OXIDATION-DEHYDROGENATION | | | |
| Steam, 400 psig | | | 4.271 lb | Steam, 400 psig | | | 9.64 lb |
| 150 psig | | | — | 150 psig | | | — |
| 30 psig | | | .143 lb | 30 psig | | | −2.17 lb |
| Power, kwh | | | 0.0477 | Power, kwh | | | 0.0124 |
| Cooling Water, gal. | | | 13.08 | Cooling Water, gal. | | | 12.05 |
| Fuel, BTU | | | 3215.0 | Fuel, BTU | | | −10.35 |
| Condensate, lb | | | −4.9 | Condensate, lb | | | −10.35 |
| Fuel Credits | | | −216.0 | Fuel Credits | | | — |
| VI. TOTALS | UNIT/lb | BTU/lb[2] | BTU/lb | VI. TOTALS | UNIT/lb | BTU/lb[2] | BTU/lb |
| Steam, 400 psig | 4.491 × | 1375 = | 6179 | Steam, 400 psig | 9.64 × | 1375 = | 13255 |
| 150 psig | 2.413 × | 1290 = | 3115 | 150 psig | 4.312 × | 1290 = | 5563 |
| 30 psig | 0.247 × | 1220 = | 301 | 30 psig | −1.25 × | 1220 = | −1525 |
| Power kwh | 0.0607 × | 12437 = | 755 | Power, kwh | 0.0556 × | 12437 = | 692 |
| Cooling Water, gal. | 24.41 | | | Cooling Water, gal. | 31.28 | | |
| Fuel, BTU | 3175.0 | | 3175 | Fuel, BTU | 3221.0 | | 3221 |
| Condensate, lb | −7.02 × | 130 = | −912 | Condensate, lb | −15.5 × | 130 = | −2015 |
| TOTAL BTU/lb | | | 12613 | TOTAL BTU/lb | | | 19191 |

[1]All data expressed in units/pound of butadiene.
[2]Assigned energy values used throughout the examples.

What is claimed is:

1. A process for separating and producing $C_n$ dienes from a $C_n$ hydrocarbon feed stream comprising $C_n$ alkynes, $C_n$ n- and isoalkenes, $C_n$ n- and isoalkanes and $C_n$ dienes, wherein n is between 4 and 8 inclusive, the process comprising:
   a. hydrogenating the $C_n$ hydrocarbon feed stream to produce a substantially $C_n$ alkyne-free stream comprising $C_n$ n- and isoalkenes, $C_n$ n- and isoalkanes, $C_n$ dienes and heavy residues;
   b. removing the heavy residues from the $C_n$ alkyne-free stream to produce a purified $C_n$ stream;
   c. separating the purified $C_n$ stream in a first separation zone to produce an extract stream comprising the $C_n$ dienes and a raffinate stream comprising the $C_n$ n- and isoalkenes and the $C_n$ n- and isoalkanes;
   d. removing the $C_n$ isoalkenes from the raffinate stream and passing a remaining raffinate stream comprising $C_n$ n-alkenes and $C_n$ n-isoalkanes to a second separation zone;
   e. separating the remaining raffinate stream in the second separation zone to produce a $C_n$ alkane stream comprising $C_n$ n- and isoalkanes and a $C_n$ alkene stream comprising $C_n$ n-alkenes; and
   f. converting the $C_n$ alkene stream into a $C_n$ diene stream and recycling said $C_n$ stream to the first separation zone.

2. The process of claim 1 wherein n is 4, the $C_n$ n- and isoalkenes are 1-, 2- and isobutene, the $C_n$ n- and isoalkanes are n- and isobutane, and the $C_n$ dienes are 1,2- and 1,3-butadiene.

3. The process of claim 2 wherein the hydrogenating comprises contacting the $C_4$ hydrocarbon feed stream with hydrogen in the presence of a hydrogenation catalyst.

4. The process of claim 3 wherein the removing of heavy residues comprises extracting the heavy residues with a selective solvent.

5. The process of claim 4 further comprising water-washing the purified $C_4$ stream to remove carbonyls therefrom prior to separating the purified $C_4$ stream into the extract and raffinate streams.

6. The process of claim 5 wherein the separating of the purified $C_4$ stream into the extract and raffinate streams comprises extracting the 1,2- and 1,3-butadienes with a selective solvent.

7. The process of claim 6 further comprising water-washing of the raffinate stream prior to removing the isobutene therefrom.

8. The process of claim 7 wherein the removing of the isobutene from the raffinate stream comprises oligomerizing the isobutene with an oligomerizing amount of 1-butene in an oligomerization zone.

9. The process of claim 8 wherein the converting of the butene stream to the butadiene stream comprises contacting the butene stream with steam, an oxygen-containing gas and carbon monoxide at a steam:gas:carbon monoxide:butene mass ratio between about 3.5:1.0:0.1:1.0 and about 4.0:1.3:0.2:1.0 at a temperature between about 1080° and about 1180° F and a pressure between about 1 and about 2 atmospheres.

10. The process of claim 8 wherein the converting of the butene stream to the butadiene stream comprises contacting the butene stream with steam at a steam:butene mass ratio between about 0.7:1.0 and about 1.5:1.0 at a temperature between about 1480° and about 1590° F and a pressure between about 1.5 and about 2 atmospheres.

* * * * *